United States Patent
Hilbrig et al.

(10) Patent No.: US 7,378,238 B2
(45) Date of Patent: May 27, 2008

(54) METHOD FOR TREATING BIOMASS FOR PRODUCING CELL LYSATE CONTAINING PLASMID DNA

(75) Inventors: Frank Hilbrig, Bayreuth (DE); Ruth Freitag, Bayreuth (DE); Ivo Schumacher, Jona (CH)

(73) Assignees: DrM, Dr. Mueller AG, Maennedorf (CH); Polytag Technology SA, Lausanne (CH)

( * ) Notice: Subject to any disclaimer, the term of this patent is extended or adjusted under 35 U.S.C. 154(b) by 552 days.

(21) Appl. No.: 10/415,893

(22) PCT Filed: Dec. 24, 2001

(86) PCT No.: PCT/CH01/00741

§ 371 (c)(1),
(2), (4) Date: May 6, 2003

(87) PCT Pub. No.: WO02/057446

PCT Pub. Date: Jul. 25, 2002

(65) Prior Publication Data

US 2004/0014098 A1   Jan. 22, 2004

(30) Foreign Application Priority Data

Jan. 19, 2001   (CH) .................................... 0080/01

(51) Int. Cl.
 *C12Q 1/68* (2006.01)
 *C07H 21/02* (2006.01)
(52) U.S. Cl. .......................................... 435/6; 536/23.1
(58) Field of Classification Search ................... 435/6; 536/23.1
See application file for complete search history.

(56) References Cited

U.S. PATENT DOCUMENTS

| | | | |
|---|---|---|---|
| 5,234,809 A | 8/1993 | Boom et al. .................... | 435/6 |
| 5,247,699 A | 9/1993 | Hartman ......................... | 435/6 |
| 6,673,631 B1 * | 1/2004 | Tereba et al. ................ | 436/526 |
| 6,797,476 B2 * | 9/2004 | Lander et al. ................. | 435/6 |

FOREIGN PATENT DOCUMENTS

| | | |
|---|---|---|
| EP | 0 648 776 A | 4/1995 |
| EP | 0 696 638 A | 2/1996 |
| EP | 0 795 602 A | 9/1997 |
| EP | 0 814 156 A | 12/1997 |
| GB | 1082862 | 9/1967 |
| WO | 92 07863 A | 5/1992 |
| WO | 95 14768 A | 6/1995 |
| WO | 96 36706 A | 11/1996 |
| WO | WO 9636706 A1 * | 11/1996 |
| WO | WO 99/57931 | 11/1999 |

OTHER PUBLICATIONS

Wang B et al: "Large-Scale Preparation of Plasmid DNA . . . " Biotechniques, vol. 18, No. 4, Apr. 1995, pp. 554-555.
Yamaguchi et al XP000588449 IEICE Transactions on Communications, Institute of Electronics Information and Comm. Eng. . vol. E79-B, No. 3, Mar. 1996, pp. 266-271 "Proposal of Multi Layered Microcell System with no Handover Areas".
Shin et al., IEEE TENCON 1999; Power Control and QoS of a CDMA based Hierarchical Cell Structure Network, pp. 1220-1223.
Isidoro Feliciello et al: "A Modified Alkaline Lysis Method . . . " in Analytical Biochemistry 212, pp. 394-401, 1993.
Gerd Romanowski: "Adsorption of Plasmid DNA to Mineral Surfaces and Protection . . . " in Applied and Environmental Microbiology, Apr. 1991, pp. 1057-1061.
Alfred Carlson et al: "Mechanical Disruption of *Escherichia coli* . . . " in Biotechnology and Bioengineering, vol. 48, pp. 303-315, 1995.

* cited by examiner

*Primary Examiner*—Suryaprabha Chunduru
(74) *Attorney, Agent, or Firm*—Michael J. Striker

(57) ABSTRACT

The method of making the clear cell lysate containing plasmid DNA from a biomass obtained in a cell culture process includes filtering the biomass obtained in the cell culture process with a filter medium in the presence of diatomaceous earth acting as a filtering agent to form a filter cake containing the biomass and the filter medium, then thermally digesting the biomass in the filter cake to form a cell lysate containing the plasmid DNA and filtering the cell lysate to form a clear filtrate. The clear filtrate contains the plasmid DNA and has a clarity characterized by an $OD_{600}$ of at maximum 0.05 U/cm.

4 Claims, No Drawings

METHOD FOR TREATING BIOMASS FOR PRODUCING CELL LYSATE CONTAINING PLASMID DNA

BACKGROUND OF THE INVENTION

The present invention relates to a method for the integrated treatment of biomass from a cell culture process for producing clear cell lysate containing plasmid DNA, and a plasmid DNA cell lysate produced by the method.

Treatment is to be understood as meaning a conditioning method for providing clear cell lysate containing plasmid DNA. An integrated method is to be understood as meaning a method in which the individual steps of the method are contiguous with one another so that the product stream is conveyed virtually continuously. The basically multistage method can be carried out continuously or batchwise.

The separation of biological material from a cell culture process, the digestion of the biological material and the production of a clear cell lysate containing plasmid DNA is a customary method in the area of molecular biology. In the known methods, biological material, for example comprising E. coli bacteria cells, is separated from the culture supernatant, resuspended and then digested. Separating off the solid constituents gives a clear cell lysate which contains the plasmid DNA in addition to genomic DNA, RNA, proteins and endotoxins.

It is known that biological materials can be separated from the cell culture process by batchwise or continuous centrifuging. The separation of baker's yeast cells by filtration over a bed of filtering agent is described in GB-A-1082862. Said patent also discloses the separation of cell residues from a yeast autolysate by means of a filtering agent.

The customary methods for cell digestion are the known alkaline lysis and thermal lysis. In order to improve the cell digestion, enzymes, for example lysozyme, and/or detergents are frequently added to the cell suspension. In the alkaline lysis method, a precipitate which substantially contains the cell debris and parts of the genomic DNA and of the protein is obtained after the cell digestion at pH 12 by addition of sodium hydroxide solution and sodium dodecylsulphate and subsequent neutralization with a high molecular weight acetate buffer. The complete isolation of this precipitate can be achieved only by thorough centrifuging. A centrifugal acceleration of 12000 g is not sufficient for this purpose (I. Feliciello et al., Anal. Biochem. 212 (1993) 394-401). The precipitate can be very substantially isolated only at a centrifugal acceleration of 26000 g for 30 minutes at 4° C. On the other hand, the filtration of this precipitate is associated with low process rates and large losses of plasmid DNA, even with the aid of very fine filtering agents or in combination with a flotation step. The adsorption of plasmid DNA on the surface of the filtering agent contributes considerably to the losses. In particular, plasmid DNA binds very rapidly and strongly to such mineral surfaces if the concentration of divalent cations exceeds 0.1 mmol or the monovalent cations exceed 20 mmol in the case of potassium or 50 mmol in the case of sodium (G. Romanowski et al., Appl. Environ. Microbiol. 57 (1991) 1057-1061).

High molecular weight nucleic acids are sensitive to hear forces. Strong shear forces can lead to irreversible damage to nucleic acids, in particular to breaks in the strand. For this reason, mechanical digestion methods are seldom used for nucleic acid treatment (A. Carlson et al., Biotechnol. Bioeng. 48 (1995) 303-315). It is also known that, in industrial centrifuges with continuous introduction of liquid, high shear forces at the rotor inlet act on the nucleic acids and inevitably lead to breaks in the strand.

WO 96/36706 describes a method in which microorganisms are digested in the presence of detergents (Triton®) and by heating to 70° C. to 1000° C. in a flow-through heat exchanger. This is a combination method comprising thermolysis and with a detergent (optionally with lysozyme). In the absence of lysozyme, a thermal treatment for 30 seconds is described; in the presence of lysozyme, a thermal treatment for 6 seconds is described. On cell digestion by heating, solid compounds comprising debris, genomic DNA and proteins form. In addition, very substantial denaturing of DNA-degrading enzymes, so-called DNases, may be assumed as a result of the heat treatment. A clear cell lysate is obtained after batchwise centrifuging. In this method, only the cell digestion is carried out continuously, the solid constituents being separated off batchwise by centrifuging. In order to obtain the final clear cell lysate, a filtration over a membrane filter also had to be carried out after the centrifuging.

According to WO 92/207863 an apparatus and a method for isolation of nucleic acids from cell suspensions are known. According to this, the cells are immobilized in the cavities of an upstream, porous matrix in the form of a layer. This is achieved by deep filtration in the matrix, by virtue of the fact that the cavity size is of the order of magnitude of the cells and the matrix surface has ion exchange properties. The particle size of the matrix is 10 to 50 μm. Owing to the ion exchange properties, DNA is adsorbed on the matrix surface. The invention does not relate to adsorption of DNA. The known method gives purified DNA but not a clear cell lysate containing plasmid DNA.

EP-A-0814156 describes a method for purifying DNA. The kieselguhrs used therein are not specified. The lysis is affected by the alkaline method. Thermal lysis is not described.

The prior art thus discloses neither methods which make it possible to work up large amounts of biomass in an integrated manner nor methods by means of which large amounts of clear cell lysates containing plasmid DNA can be provided by an integrated procedure.

There is a need for an efficient conditioning method for providing clear cell lysate containing plasmid DNA from a cell culture process which permits plasmid DNA purification.

SUMMARY OF THE INVENTION

It is therefore the object of the present invention to provide an integrated working-up method which makes it possible to provide large amounts of clear cell lysates with high plasmid DNA yield from a biomass in an efficient and controlled manner while avoiding the disadvantages of the alkaline lysis method and of centrifuging.

This object is achieved, according to the invention, if in each case filtration is affected in a first stage in a filter in the presence of a filtering agent, the biomass contained in the filter cake is thermally digested in a second stage and the cell lysate is filtered in a further stage.

It has now been found that any volume from 50 ml to 10000 l of biomass can be rapidly processed to give clear cell lysate containing the plasmid DNA by the method of the present invention. Particularly advantageous is the fact that, in the method of the present invention, the applied excess pressure during filtration provides a check with regard to the shear forces acting on the nucleic acids. In particular, after separation by gel electrophoresis, a cell lysate produced according to the invention clearly shows the bands for plasmid DNA, in addition to the bands for genomic DNA and RNA, without detectable damage to the nucleic acids due to breaks in the strand. Moreover, the cell lysate obtained is freed from unpleasant odours by the heat treatment.

DESCRIPTION OF THE PREFERRED EMBODIMENTS

It is expedient that the filtering agent is present during the digestion. This has the advantage that the filtering agent required for the subsequent clarifying filtration of the cell lysate is already present. The continuous use of the same filtering agent over all steps (isolation, digestion, clarification) is also efficient in terms of process engineering and therefore economical. It is particularly advantageous if, instead of suspending the filter cake for the lysis, combined thermal digestion and clarifying filtration are carried out directly in the existing filter cake (for example by pumping through hot lysis buffer) and thus very clear cell lysate can be obtained directly. Consequently, the entire method is more efficient and hence economically more advantageous as a result of the reduction of the number of individual steps.

The choice of the filtering agent is of decisive importance. The filtering agent must be inert in order to minimize adsorption effects. It has proved expedient to use, as the filtering agent, calcined kieselguhrs having an $SiO_2$ content of at least 90% by weight and additionally having the following properties:

Wet density: 0.2-0.4 g/cm$^3$
Permeability: 0.02-2 Darcy
BET surface area: 2-20 m$^2$/g
Geometrical surface area: 0.25-0.65 m$^2$/g
Particle size: 2.5-8.0 µm
Particle size retention (99%): 0.1-2 µm This has the advantage that very clear filtrate having a sufficiently high filtration flow rate at moderate differential pressure is obtained in one filtration step. In addition to this combination of efficiency and effectiveness, the use of highly pure filtering agents has the advantage that their surfaces are standardized and hence their properties can be controlled.

It is also expedient that the same filtering agent is used in all stages. This has the advantage that the individual steps of the method are contiguous with one another so that the product stream is conveyed virtually continuously.

The amount of filtering agent, based on the solids content of the solution to be filtered, the filtration area and the level of the maximum excess filtration pressure to be applied can only be determined empirically.

It has proved particularly expedient to carry out the digestion thermally. This has the advantage that the digestion can be carried out under mild conditions, for example in the physiological pH range, under very readily controllable and reproducible conditions. The process rate can be considerably increased if a flow-through heat exchanger is used instead of the batchwise heating of the cell suspension. It may also be assumed that a part of the DNA-degrading enzyme is deactivated on heating. In comparison with the alkaline lysis, the odour annoyance in thermal lysis is substantially lower.

The digestion is carried out at temperatures between 70° C. and 90° C., preferably at 70° C. to 85° C., in particular at 80° C. At a temperature of less than 70° C., the thermal digestion is incomplete; at a temperature above 90° C., plasmid DNA melts. The duration of the thermal treatment can only be determined empirically.

It is 30 seconds to a few minutes.

The digestion must be carried out at a pH between 7 and 10. In this pH range, the adsorption losses of plasmid DNA are minimal and the activity of lysozyme is optimal. Moreover, plasmid DNA is already present in the physiological pH range in the clear cell lysate obtained.

It is expedient to carry out the digestion in the presence of exclusively monovalent cations. This has the advantage that losses in the final filtration to give the clear plasmid DNA lysate owing to adsorption on the surface of the filtering agent are minimal. Polyvalent cations which are liberated during the cell digestion are masked by complexing agents.

The maximum concentration of cations should be not more than 20 mmol for $K^+$, not more than 50 mmol for $Na^+$ or not more than 150 mmol for $NH_4^+$. When these maximum concentrations are exceeded, losses of plasmid DNA occur owing to adsorption on the surface of the filtering agent. If a plurality of cation species are present, the additive nature of the effect must be taken into account when specifying the permissible total concentration.

Clear cell lysate containing plasmid DNA is distinguished by a clarity $OD_{600}$ of not more than 0.05 U/cm, corresponding to a decrease in the turbidity of at least 99%. The resulting clear cell lysate with the plasmid DNA can be used for cloning, for transformation, for transfection, for microinjection into cells, for gene therapy, for DNA vaccination and/or for polymerase chain reaction (PCR).

The invention is to be described in more detail with reference to examples.

EXAMPLES

Example 1

Plasmid DNA pHEN1 (4618 bp) in the *E. coli* strain TG1 was multiplied in 2TY medium at 37° C. for 16 hours in a shaken flask. 15, 30 or 60 g/l of CelpureP300® (trade mark of World Minerals Inc.) were added to three *E. coli* suspensions of 125 ml each ($OD_{600}$=6) and stirring was carried out continuously at 20° C. Each suspension was then transferred to a suction filter (10 cm$^2$ filter area, 200 ml capacity) in which a prefilter cake of 2 kg/m$^2$ of CelpureP3000® had been built up beforehand over a filter medium comprising polypropylene monofilament (pore size 10 µm). The filtration was carried out at an excess pressure of 0.5 bar and 20° C.

In all cases, a clear filtrate was obtained. The highest mean filtration flow rate (2.8 m$^3$/m$^2$ h) was achieved with 30 g/l of CelpureP300®. The results are summarized in Table 1.

TABLE 1

| CelpureP300 ®(*) in g/l | Mean filtration flow rate (m$^3$/m$^2$h) | $OD_{600}$ of the filtrate (U/cm) | Decrease in turbidity in % |
|---|---|---|---|
| 60 | 1.8 | 0.04 | 99 |
| 30 | 2.8 | 0.05 | 99 |
| 15 | 2.4 | 0.03 | 99 |

(*)Properties: Silica content: 98.65%; wet density: 0.26 g/cm$^3$. Permeability: 0.15-0.30 Darcy; BET surface area: 4-6 m$^2$/g; geometrical surface area: 0.62 m$^2$/g; particle size retention (99%): 0.6-0.75 µm.

Example 2

Lysis Buffer A:

150 mmol of Tris.HCl, 25 mmol of Na$_2$EDTA, 8% by weight of sucrose (pH 9)

Lysis buffer B:

As for lysis buffer A, but additionally 2% of TritonX-100® (trade mark of Rohm und Haas)

Two filter cakes from Example 1 with 30 g/l of CelpureP300® were each resuspended in 190 ml of lysis buffer A or B. 500 U/ml of lysozyme were added in each case and the suspensions were heated to 80° C. for 30 seconds with continuous stirring. The still hot suspensions were transferred to a suction filter in which a prefilter cake of 2 kg/m$^2$ of CelpureP300® (incubated for 15 minutes in the corresponding lysis buffer) had been built up over a filter medium comprising polypropylene monofilament (pore size 10 µm). The filtration was carried out at 0.5 bar excess pressure.

By means of the lysate buffer A, a clear cell lysate (OD$_{600}$=0.02) with a mean filtration flow rate of 0.4 m$^3$/m$^2$ h was obtained. In contrast, the mean filtration flow rate was reduced by 50% by the addition of Triton X-100® (lysis buffer B). A significant increase in the mean filtration flow rate to 1.5 m$^3$/m$^2$ h in the lysis buffer A was achieved when the total amount of CelpureP300® ad been adjusted to 100 g/l and when PVDF warp/PTFE weft monofilament (pore size 11.5 µm) had been used as the filter medium.

Example 3

3.7 ml of λ DNA (*E. coli*; 48.5 kb dsDNA; 0.51 mg/ml) were added to 25 ml of a buffer solution consisting of 250 mmol of Tris.HCl, 25 mmol of Na$_2$EDTA and 8% by weight of sucrose (pH 9.09). 0.75 g of CelpureP300® (30 g/l) was added and the suspension was shaken for 30 minutes at 20° C. and 200 rpm.

UV absorption measurements at 260 nm and a PicoGreen® test (kit from Molekular Probes Inc.) showed no difference between the λ DNA concentration in the supernatant of the suspension and the concentration in the starting solution.

Example 4

*E. coli* cells DH5α with the plasmid DNA pEGFP-N1 were divided into four equal parts and each part suspended in a buffer consisting of Tris.HCl and 10 mM EDTA. From one of these suspensions, the cells were digested using the Nucleobond® AX kit (trade mark of Macherey-Nagel) by the alkaline lysis method, and the plasmid DNA was isolated and purified. In the case of the other three suspensions, the cells were thermally digested for 5 minutes at 70° C./pH 9, 70° C./pH 10 and 60° C./pH 10, and the plasmid DNA was isolated and purified in each case using the same kit. The plasmid DNA quantification of the four samples by means of the PicoGreen test showed that the digestion by the alkaline lysis method and the thermal lysis at 70° C. and pH 9 or pH 10 led to the same yields of the plasmid DNA, whereas the thermal digestion at 60° C. and pH 10 gave only about 30% of the yield of the plasmid DNA obtained by the other three methods. From Example 3, it is known that no adsorption of the plasmid DNA on the surface of the filtering agent is to be expected under the thermal lysis conditions described.

Method of Measurement:

Clarity Measurement

The clarity of a filtrate (optical density, OD) was determined using a Lambda 20 UV/Vis spectrometer from Perkin-Elmer in the absorption mode at 600 nm and a wavelength of 1 cm against water as reference at room temperature.

The invention claimed is:

1. A method of making a clear cell lysate containing plasmid DNA from a biomass obtained in a cell culture process, said method consisting of the steps of:
    a) suspending the biomass together with a filtering agent to form a first suspension, wherein the filtering agent is a kieselguhr and said kieselguhr contains greater than or equal to 90% silica, a wet density of 0.2 to 0.4 g/cm$^3$, a permeability of 0.02 Darcy, a BET surface area of 2 to 20 m$^2$/g, a geometrical surface area of 0.25 to 0.65 m$^2$/g, a particle size of 2.5 to 8.0 µm, and a 99% particle size retention of 0.1 to 0.2 µm;
    b) filtering the first suspension in the presence of the filtering agent with a filter medium to form a filter cake containing said biomass;
    c) after the filtering of step b), re-suspending the filter cake formed during said suspending in a lysis buffer at pH 7 to 10 to form a second suspension, wherein the lysis buffer consists of 150 mmol of Tris-HCL, 25 mmol of Na$_2$EDTA, 8% by weight of sucrose, and optionally containing 2% TritonX-100®;
    d) heating said second suspension at temperatures between 70° C. to 90° C. for at least 30 seconds to thermally digest said biomass;
    e) after the heating of step d), filtering said second suspension with the filter medium in the presence of the filtering agent to obtain the cell lysate;
wherein said filtering of said second suspension and said first suspension consists of filtering only with the aid of vacuum or pressure;
    f) filtering the cell lysate to form a clear filtrate containing said plasmid DNA and having a clarity OD$_{600}$ of not more than 0.05 U/cm, which corresponds to a decrease of turbidity of at least 99%, and
in which said method does not include centrifugation.

2. The method as defined in claim 1, wherein said filter agent is diatomaceous earth.

3. A method of making a clear cell lysate containing plasmid DNA from a biomass obtained in a cell culture process, said method consisting of the steps of:
    a) suspending the biomass together with a filtering agent to form a first suspension, wherein the filtering agent is a kieselguhr and said kieselguhr contains greater than or equal to 90% silica, a wet density of 0.2 to 0.4 g/cm$^3$, a permeability of 0.02 Darcy, a BET surface area of 2 to 20 m$^2$/g, a geometrical surface area of 0.25 to 0.65 m$^2$/g, a particle size of 2.5 to 8.0 µm, and a 99% particle size retention of 0.1 to 0.2 µm;
    b) filtering the first suspension in the presence of the filtering agent with a filter medium to form a filter cake containing said biomass; and
    c) pumping a hot lysis buffer having a pH of 7 to 10 and a temperature of from 70° C. to 90° C. through said filter cake in order to thermally digest said biomass contained in said filter cake to form a cell lysate and to perform a clarification filtration of the cell lysate simultaneously to obtain a clear filtrate, said clear filtrate containing said plasmid DNA and having a clarity OD$_{600}$ of not more than 0.05 U/cm, which corresponds to a decrease of turbidity of at least 99%, wherein the lysis buffer consists of 150 mmol of Tris-HCL, 25 mmol of Na$_2$EDTA, 8% by weight of sucrose, and optionally containing 2% TritonX-100®, and in which said method does not include centrifugation.

4. The method as defined in claim 3, wherein said filter agent is diatomaceous earth.

* * * * *